United States Patent [19]

Horn

[11] Patent Number: 5,792,115
[45] Date of Patent: Aug. 11, 1998

[54] APPARATUS AND METHOD FOR ANCHORING A CATHETER TO THE BODY OF AN INDIVIDUAL

[76] Inventor: John Russell Horn, 402 Timberline Ct., Pleasant Hill, Calif. 94523

[21] Appl. No.: 846,356

[22] Filed: Apr. 30, 1997

[51] Int. Cl.⁶ .................................................. A61M 5/32
[52] U.S. Cl. ................................................. 604/174
[58] Field of Search .................................. 604/174, 175, 604/180; 606/222–228, 333; 128/DIG. 26

[56] References Cited

U.S. PATENT DOCUMENTS

| | | | |
|---|---|---|---|
| 3,825,010 | 7/1974 | McDonald | 128/337 |
| 3,918,446 | 11/1975 | Buttaravoli | 604/180 |
| 4,164,943 | 8/1979 | Hill et al. | 128/348 |
| 4,345,601 | 8/1982 | Fukuda | 128/339 |
| 4,535,764 | 8/1985 | Ebert | 128/335 |
| 4,559,039 | 12/1985 | Ash et al. | 604/175 |
| 4,683,895 | 8/1987 | Pohndorf | 604/174 |
| 4,798,595 | 1/1989 | Andersson et al. | 604/174 |
| 4,897,082 | 1/1990 | Erskine | 604/180 |
| 4,981,475 | 1/1991 | Haindl | 604/174 |
| 5,002,563 | 3/1991 | Pyka et al. | 606/222 |
| 5,192,274 | 3/1993 | Bierman | 604/180 |
| 5,222,976 | 6/1993 | Yoon | 606/223 |
| 5,259,846 | 11/1993 | Granger et al. | 606/224 |
| 5,306,256 | 4/1994 | Jose | 604/180 |
| 5,637,098 | 6/1997 | Bierman | 604/180 |
| 5,683,417 | 11/1997 | Cooper | 606/223 |

*Primary Examiner*—Manuel Mendez
*Attorney, Agent, or Firm*—Thomas R. Lampe

[57] ABSTRACT

A system for anchoring a catheter to the body of an individual wherein one or more rigid attachment members forming closed loops are secured to the body by detachable surgical needles. A catheter mounting member is connected to the attachment member or attachment members to engage a catheter and restrict movement of the catheter relative to the attachment member or members and relative to the individual.

8 Claims, 4 Drawing Sheets

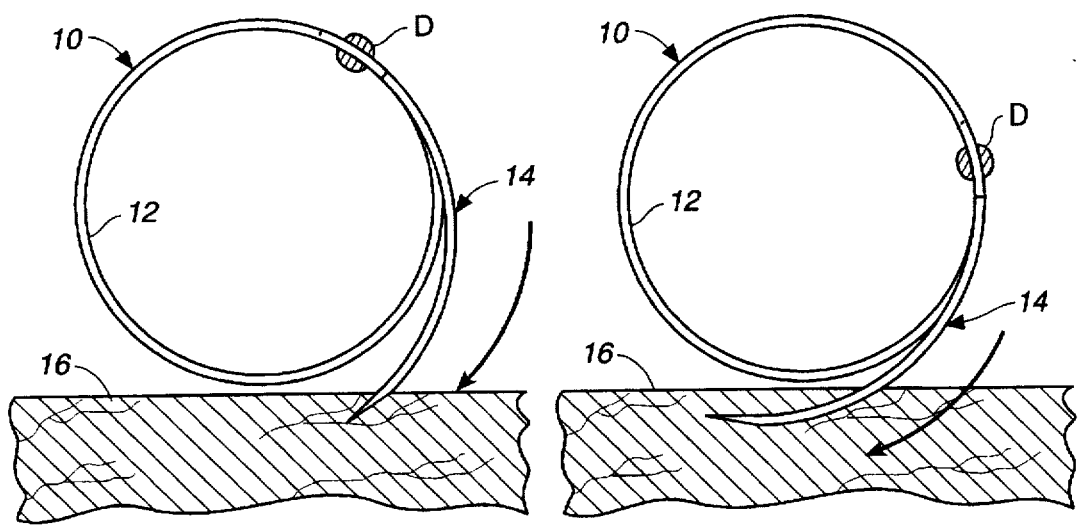
FIG._1A  FIG._1B
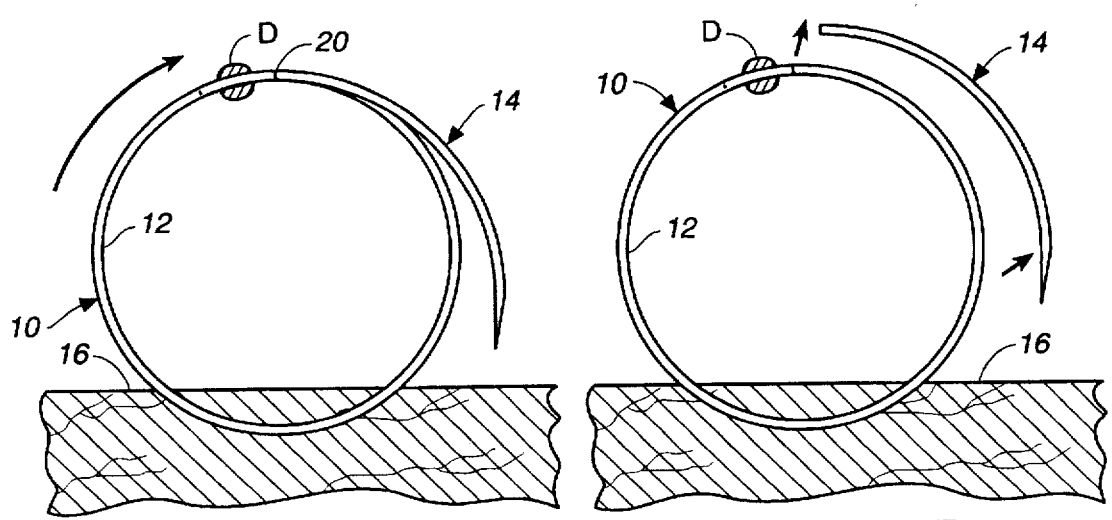
FIG._1C  FIG._1D
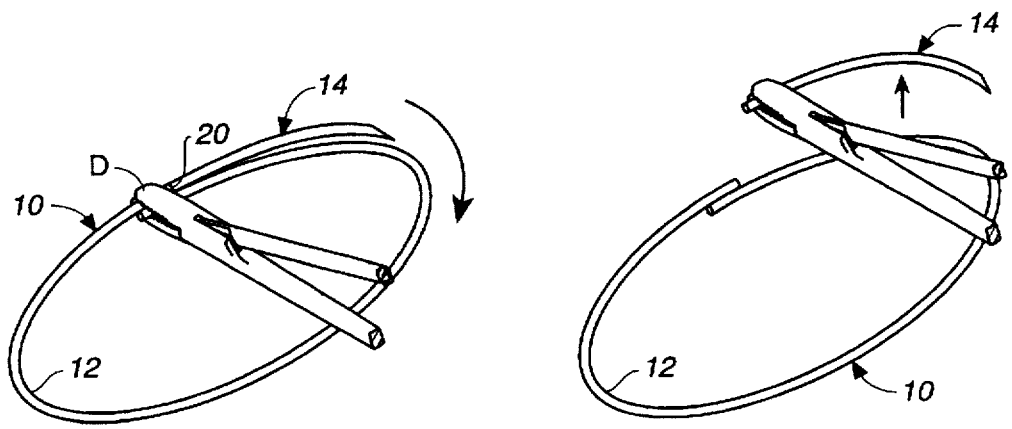
FIG._2A  FIG._2B

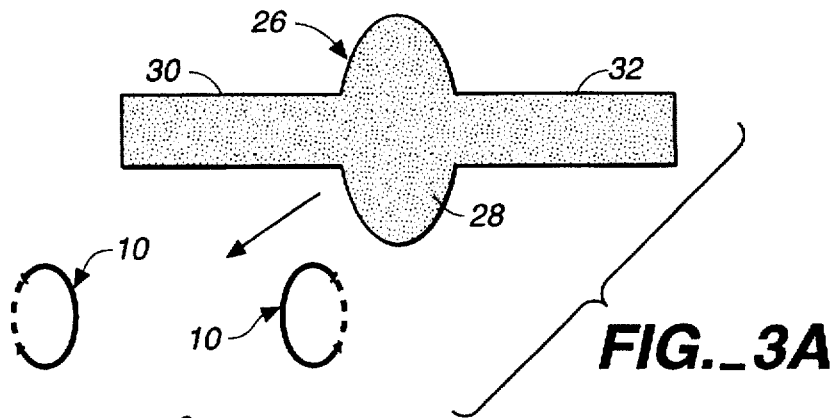
FIG._3A
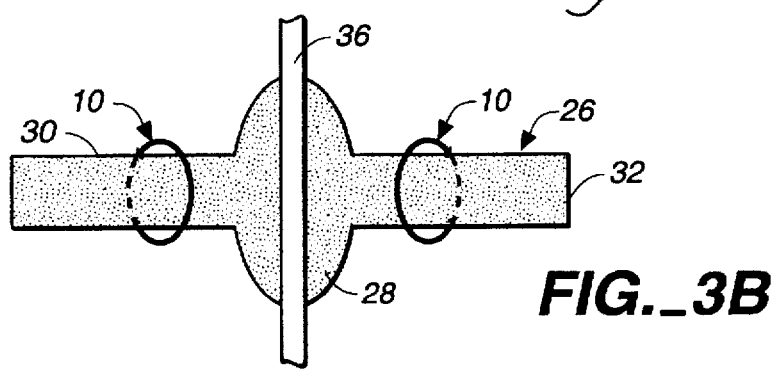
FIG._3B
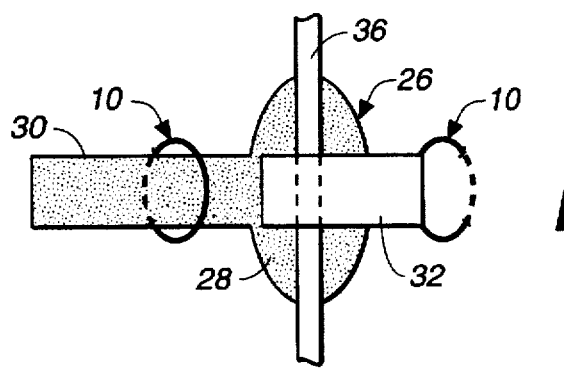
FIG._3C
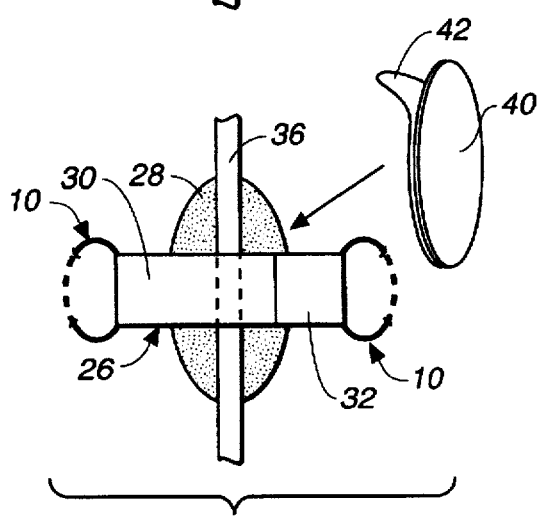
FIG._3D
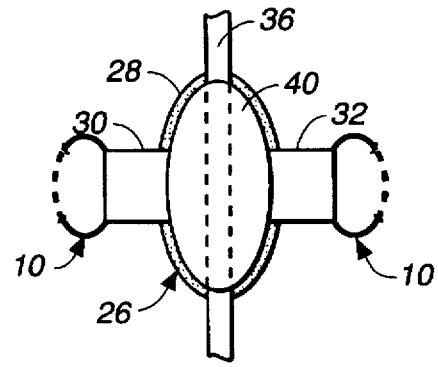
FIG._3E

*FIG._4*
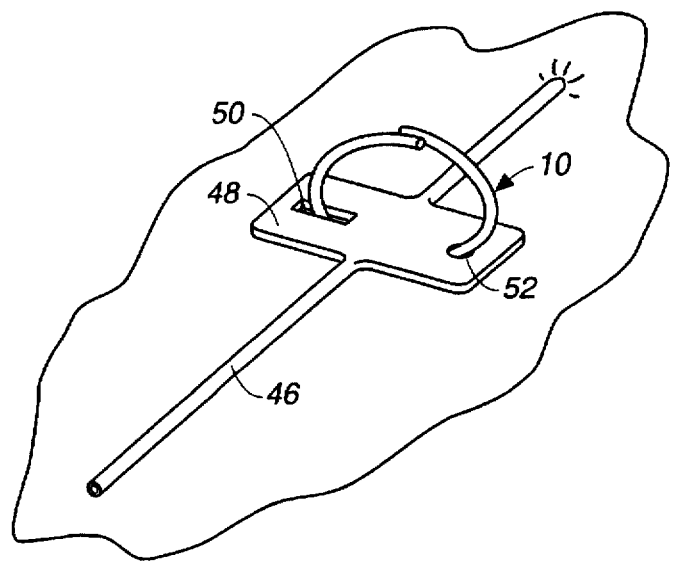
*FIG._5A*
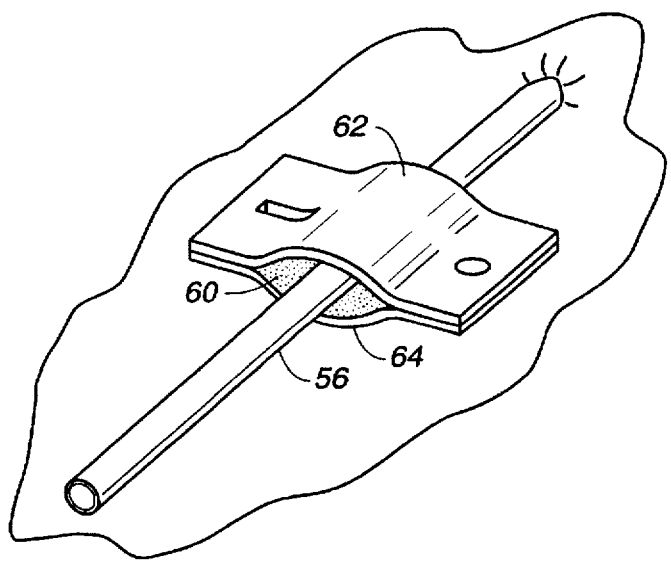
*FIG._5B*
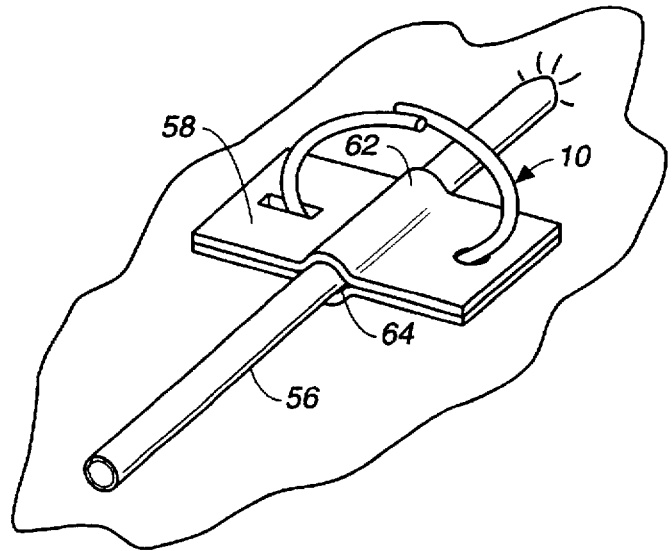

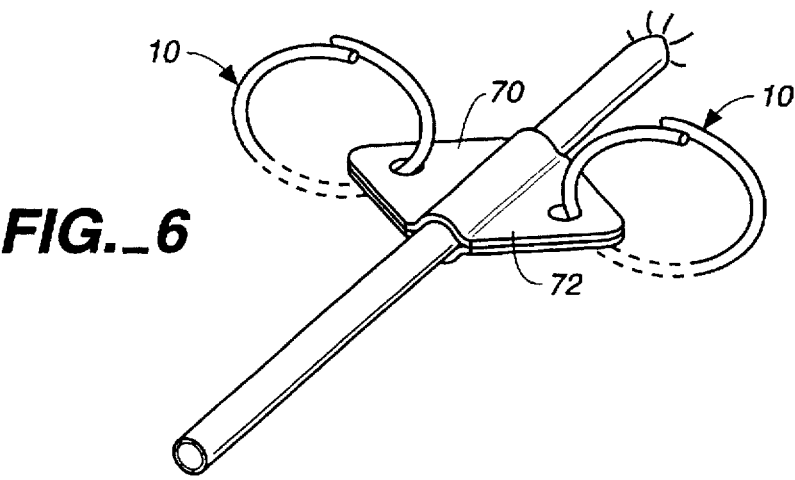
FIG._6
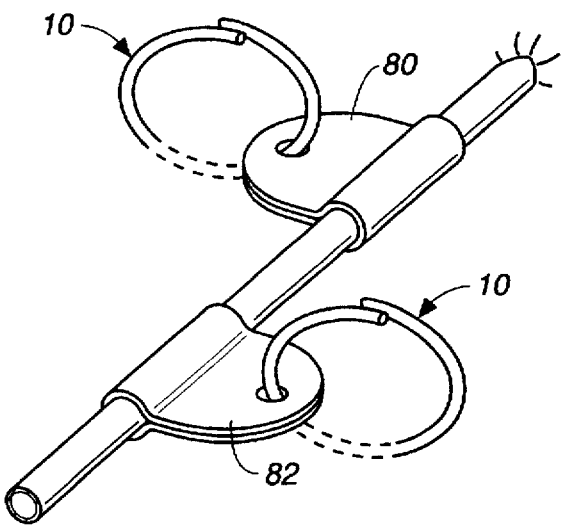
FIG._7
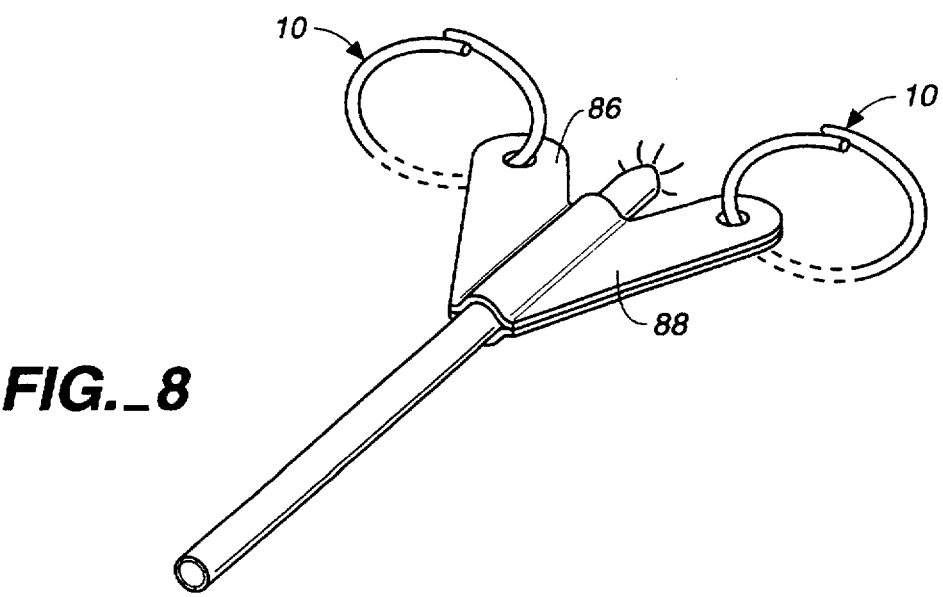
FIG._8

APPARATUS AND METHOD FOR ANCHORING A CATHETER TO THE BODY OF AN INDIVIDUAL

TECHNICAL FIELD

This invention relates to a catheter anchoring system, more particularly, to an apparatus and a method for anchoring a catheter to the body of an individual.

BACKGROUND OF THE INVENTION

Catheters are commonly employed in the treatment or care of patients. A catheter is inserted into a patient's body and is usually employed to either supply fluids to the individual or drain fluids therefrom.

It is very important to prevent a catheter from being inadvertently dislodged or removed from the patient's body. Accidental dislodgement of a catheter can severely adversely impact the health of the patient and in some situations can even result in a patient's death. Then too, it is sometimes difficult, if not impossible, to reinsert a catheter in a patient at the correct position once removal of the catheter has occurred.

A number of prior art approaches exist having the object of preventing accidental or inadvertent removal of a catheter from a patient's body. It is known, for example, to employ catheter holders which clamp or frictionally engage a catheter, the holder itself being sutured to the skin. Such an approach is time consuming. Furthermore, sutures tend to draw skin tight and can lead to infections. Furthermore, a patient may development an allergic reaction to the suture material itself, presenting additional complications.

Adhesive has also been employed to attach a catheter holder to an individual's skin. Adhesive tape has also been utilized to secure a catheter directly to the skin. Unfortunately, adhesive is not always effective since perspiration, urine or other liquids can weaken or break the bond with the skin. Furthermore, after time, skin will tend to exfoliate from the patient, also rendering the adhesive ineffective.

Prior art holders employed in an attempt to anchor a catheter to a patient typically define constrictive openings through which the catheters pass, frictional and clamping forces applied to the catheters by the holders being utilized to resist movement of the catheter. Not only are such arrangements less than effective from the standpoint of positively holding the catheter in place, a constrictive-type holder can pinch and deform the catheter held thereby and diminish the size of the catheter fluid passage, thus impeding flow of fluid to or from the patient.

The following United States patents are hereby made of record and are believed to be representative of the prior art in this field: U.S. Pat. No. 4,798,595, issued Jan. 17, 1989, U.S. Pat. No. 4,683,895, issued Aug. 4, 1987, U.S. Pat. No. 4,559,039, issued Dec. 17, 1985, U.S. Pat. No. 4,345,601, issued Aug. 24, 1982, U.S. Pat. No. 4,164,943, issued Aug. 21, 1979.

There is no disclosure or suggestion in these patents of the apparatus and method for anchoring a catheter to the body of an individual in a highly effective manner as disclosed and claimed herein.

DISCLOSURE OF INVENTION

The present invention relates to an apparatus and method which are highly effective for anchoring a catheter to the body of an individual. The catheter holding system of the present invention may be quickly applied to the body of an individual and positively retains the catheter in place, even for long periods of time, without adversely affecting the well being of the patient.

The apparatus of the invention includes a substantially rigid attachment member forming a closed loop and defining an opening, the attachment member for passing through the skin of an individual at spaced skin locations to secure the attachment member to the individual with a segment of the attachment member located above the skin and a segment of the attachment member located below the skin.

A catheter mounting member is provided for connection to the attachment member and for passing through the opening of the attachment member above the skin of the individual to whom the attachment member is secured. The catheter mounting member is for engaging a catheter, for interconnecting the attachment member and the catheter, and for restricting movement of the catheter relative to the attachment member and relative to the individual.

The substantially rigid attachment member is initially detachably connected to a surgical needle at a free end of the attachment member. The surgical needle projects outwardly and away from the attachment member. The surgical needle has a pointed distal end and spaced from the attachment member for piercing the skin of an individual to attach the apparatus to the body of the individual.

The invention also encompasses a method of anchoring a catheter to the body of an individual. The method includes the step of positioning a catheter mounting member adjacent to the skin of an individual.

The catheter mounting member is then attached to the individual by passing a substantially rigid attachment member forming a loop and defining an opening through the catheter mounting member and through the skin of the individual whereby the catheter mounting member and the skin of the individual are located in the opening and secured together by the attachment member to restrict movement of a catheter connected to the catheter mounting member relative to the attachment member and relative to the individual.

Other features, advantages, and objects of the present invention will become apparent with reference to the following description and accompanying drawings.

BRIEF DESCRIPTION OF DRAWINGS

FIGS. 1A through 1D illustrate the sequential steps carried out when attaching the rigid attachment member of the present invention to the body of a patient utilizing a surgical needle detachably connected to the attachment member;

FIGS. 2A and 2B are perspective views of the attachment member and surgical needle, FIG. 2A illustrating the surgical needle attached to the attachment member and FIG. 2B illustrating the surgical needle having been removed therefrom;

FIGS. 3A through 3E illustrate a preferred form of the apparatus and show the sequential steps carried out when anchoring a catheter to the apparatus;

FIG. 4 illustrates an alternative embodiment of the apparatus anchoring a catheter to the body of an individual;

FIGS. 5A and 5B illustrate yet another embodiment of the apparatus, FIG. 5A illustrating a catheter in the process of being secured to a patient's body and FIG. 5B illustrating a subsequent condition wherein the catheter is secured in place by the apparatus; and FIGS. 6, 7 and 8 are perspective views illustrating three additional alternative embodiments of the apparatus secured to a patient's body.

MODES FOR CARRYING OUT THE INVENTION

Referring to the drawings, an attachment member in the form of a split ring 10 is shown. The ring includes overlapping ring portions, each of which terminates at a free end. The ring 10 defines an opening 12 extending through the closed loop formed by the ring.

A surgical needle 14 (FIGS. 1A through 2B) is integrally formed with the ring 10, a suitable material for such construction being stainless steel or other non-allergenic metal.

The surgical needle 14 is connected to the ring at one of the free ends thereof. The surgical needle is curved and projects outwardly and away from the ring. The distal end of the surgical needle is pointed and spaced from the ring for piercing the skin of an individual to attach the ring to the body of the individual.

FIGS. 1A through 1D illustrate the steps carried out when attaching the apparatus to the body 16 of a patient. First, as shown in FIG. 1A, the sharp point of the surgical needle 14 pierces the individual's skin. The ring and surgical needle are rotated as shown by the elongated arrows in FIGS. 1 and 2 to attain the condition shown in FIG. 1C wherein a segment of the ring 10 is located above the skin and a segment of the ring is located below the skin, the surgical needle having passed completely through the skin at two locations thereon so that some of the patient's skin is located within the opening 12. FIG. 2A also illustrates such action from a perspective view. A conventional surgical needle driver D may be employed.

A score 20 is formed at the location where the surgical needle and the ring are connected to facilitate removal of the surgical needle from the ring after the ring has been applied to the patient. This is accomplished by applying outside forces thereto. FIGS. 1D and 2B illustrate the surgical needle 14 having been broken away or detached from ring 10. Ring 10 is now securely attached to the body of the individual, the ring passing through the skin at two locations.

FIGS. 3A-3E illustrate in somewhat diagrammatic fashion the use of two split rings 10 attached to a patient's body at two different places on the body. Also illustrated is a catheter mounting member 26 which may suitably be formed, for example, from flexible plastic strip material, fabric or tape. Member 26 includes a central portion 28 and opposed end portions 30, 32 which project from central portion 28 in opposite directions.

FIG. 3A illustrates catheter mounting member 26 being placed in position relative to the two rings 10 and FIG. 3B illustrates member 26 with the end portions 30, 32 thereof projecting through the openings defined by the rings, ovoid central portion 28 being disposed between the rings. A catheter 36 is positioned in engagement with central portion 28 and then end portion 32 is folded over the catheter and the central portion as shown in FIG. 3C. A suitable adhesive is coated on the end portion 32 as well as on central portion 28 and end portion 30 (as designated by stippling) so that the end portion 32 is adhesively secured to the central portion and to the catheter.

Next, end portion 30 is folded over end portion 32, catheter 36, and central portion 28 as shown in FIG. 3D, adhesive securing the end portions together.

If desired, the adhesive pattern may be different from that shown in FIGS. 3A-3D. For example, adhesive may cover none or only part of the central portion 28. An abrasive such as sand or grit can be incorporated in the adhesive to assist the device in further resisting movement of catheter 36.

The next step is to apply a cover 40 over the end and central portions and catheter as shown FIGS. 3D and 3E. Cover 40 is preferably adhesively coated on the underside thereof, such adhesive possibly being protected by a protective sheet 42 until use of the cover is desired.

FIG. 4 illustrates another embodiment of the invention wherein a catheter 46 is integrally molded with a catheter mounting member 48 which may suitably be a plastic strip. In this arrangement, ring 10 passes through openings 50, 52 formed in member 48, opening 50 comprising a slit. It will be appreciated that a single ring 10 has been utilized to anchor the catheter 46 in place, the ring 10 having been applied, as described above, by an associated detachable surgical needle (not shown) passing both through the skin and the mounting member 48 before the needle is detached. The elongated configuration of hole 50 facilitates placement of the needle and ring relative to the mounting member.

FIGS. 5A and 5B illustrate a catheter 56 which is anchored to the body of a patient by a split ring 10 (FIG. 5B) and an alternative form of catheter mounting member 58. In this embodiment the mounting member 58 defines passageway 60 for accommodating catheters of various sizes. The member 58 includes relatively movable catheter mounting member portions 62, 64 coated internally with adhesive. These portions 62, 64 are brought together into engagement with the catheter 56 as shown in FIG. 5B to connect the mounting member 58 at a fixed location relative to the catheter. A single ring 10 connects the mounting member and catheter to the patient. Alternatively, two or more rings could be used.

FIG. 6 shows another arrangement wherein the catheter mounting member is in the form of diametrically opposed tabs 70, 72, each having a hole therein accommodating a ring 10.

FIG. 7 illustrates still another form of catheter mounting means in the form of tabs 80, 82 projecting from opposite sides of the catheter but spaced from one another along the length of the catheter.

FIG. 8 illustrates still another possible form of the catheter mounting member wherein tabs 86, 88 project diagonally relative to the catheter on opposed sides thereof. The holes are in alignment with the catheter's entrance into the skin.

It will be appreciated that the forms of catheter mounting member illustrated are representative only and that the illustrated forms are not meant to be exhaustive of the arrangements encompassed by this invention.

I claim:

1. Apparatus for anchoring a catheter to the body of an individual, said apparatus comprising, in combination:

a substantially rigid attachment member forming a substantially circular closed loop having a substantially uniform first radius of curvature and defining a substantially round opening extending through said closed loop, said attachment member having substantially uniformly curved over-lapping ring portions in registry with each other, one of said ring portions having a first free end and the other of said ring portions have a second free end, said first and second free ends being adjacent to one another with each free end positioned alongside and in close proximity to a ring portion and not projecting away from said closed loop; and a surgical needle integral with said attachment member and detachably connected to said attachment member at one of the free ends of said attachment member and projecting outwardly from and gradually diverging away from said attachment member from the free end to which said surgical needle is detachably connected, said surgical needle having a pointed distal end spaced from said attachment member for piercing the skin of an individual to attach said apparatus to the body of the individual, said surgical needle being smoothly curved over the length thereof and having a second radius of curvature larger than said first radius of curvature, and said surgical needle being in partial registry with said attachment member.

2. The apparatus according to claim 1 wherein said apparatus is scored at a location where said surgical needle and said attachment member are connected to facilitate removal of said surgical needle from said attachment member by application of outside forces to said apparatus.

3. The apparatus according to claim 1 wherein said attachment member and said surgical needle are integrally formed from stainless steel and wherein said attachment member comprises a split ring, said ring portions being in side by side engagement.

4. Apparatus for anchoring a catheter to the body of an individual, said apparatus comprising, in combination:

a substantially rigid attachment member forming a substantially circular closed loop having a substantially uniform radius of curvature and defining a substantially round opening extending through said closed loop, said attachment member for passing through the skin of an individual at spaced skin locations to secure said attachment member to the individual with a segment of the attachment member located above the skin and a segment of the attachment member located below the skin, said attachment member having closely adjacent curved over-lapping ring portions in registry with each other, one of said ring portions having a first free end and the other of said ring portions having a second free end, said first and second free ends being adjacent to one another with each free end positioned alongside and in close proximity with a ring portion and not protecting away from said closed loop; and a catheter mounting member for connection to said attachment member and for passing through the opening of said attachment member above the skin of the individual to whom the attachment member is secured, said catheter mounting member for engaging a catheter, for interconnecting said attachment member and said catheter, and for restricting movement of said catheter relative to said attachment member and relative to the individual.

5. The apparatus according to claim 4 wherein said catheter mounting member defines a plurality of mounting member openings for receiving said attachment member, at least one of said plurality of mounting member openings comprising a slit.

6. The apparatus according to claim 4 additionally comprising an adhesive having abrasive therein for adhesively securing a catheter to said catheter mounting member.

7. The apparatus according to claim 4 wherein said catheter mounting member defines a passageway for accommodating a catheter and includes a plurality of relatively movable catheter mounting member portions defining said passageway, said catheter mounting member portions comprising opposed, relatively movable ends of said catheter mounting member, and said apparatus additionally comprising a cover for covering said opposed, relatively movable ends.

8. The apparatus according to claim 4 wherein said attachment member comprises a split ring, said ring portions being in side by side engagement.

* * * * *